US008100927B2

(12) United States Patent
Lucas et al.

(10) Patent No.: US 8,100,927 B2
(45) Date of Patent: Jan. 24, 2012

(54) DERMATOME WITH ULTRASONIC CUTTING BLADE

(75) Inventors: James Raymond Lucas, Prairie Village, KS (US); Mark Loyd Jones, Chamblee, GA (US); James Earl Aldrich, Kansas City, MO (US); Peter Barrett Lucas, Olathe, KS (US); Norbert Russ, Leawood, KS (US); Shane E. Cowden, Kansas City, MO (US)

(73) Assignee: Dadson Manufacturing Corp., Grain Valley, MO (US)

( * ) Notice: Subject to any disclaimer, the term of this patent is extended or adjusted under 35 U.S.C. 154(b) by 142 days.

(21) Appl. No.: 12/323,224

(22) Filed: Nov. 25, 2008

(65) Prior Publication Data
US 2009/0138027 A1      May 28, 2009

Related U.S. Application Data

(60) Provisional application No. 60/990,867, filed on Nov. 28, 2007.

(51) Int. Cl.
*A61F 9/00*       (2006.01)
(52) U.S. Cl. ........................................ 606/166; 606/169
(58) Field of Classification Search ................. 606/131, 606/132, 166, 169, 171, 172
See application file for complete search history.

(56) References Cited

U.S. PATENT DOCUMENTS

| D401,340 S | 11/1998 | Waldman et al. |
| 6,443,969 B1* | 9/2002 | Novak et al. .................. 606/169 |
| 2004/0002722 A1 | 1/2004 | Slade |
| 2005/0154333 A1 | 7/2005 | Mulholland et al. |
| 2005/0234485 A1* | 10/2005 | Seegert et al. ................ 606/172 |

OTHER PUBLICATIONS

Rotech, Rotech Tooling Sweden (printed Jan. 19, 2009), at http://rotech.se.index.htm.
Telsonic Ultrasonics, Cut 'n' Seal (printed Jan. 19, 2009), at http://www.telsonic.com/haupt.asp?nv=2094&spr=2.
Dukane Corporation, Untrasonic Food Processing and Cutting (printed Jan. 19, 2009), at http://www.dukcorp.com/us/PFO_foodFAQ.htm.
Geiss AG, News (printed Jan. 19, 2009), at http://www.geiss-tt.com/www_geiss/ultrasoniccuttingunit_134_89_0_f.htm.
International Search Report and Written Opinion for corresponding PCT Application Serial No. PCT/US08/84906; (Opinion dated Jan. 9, 2009).

* cited by examiner

*Primary Examiner* — Ryan Severson
(74) *Attorney, Agent, or Firm* — Hovey Williamson LLP

(57) ABSTRACT

A dermatome assembly is operable to harvest a skin graft and includes an ultrasonic dermatome and a power supply. The ultrasonic dermatome includes a body and an ultrasonic blade assembly mounted in the body. The blade assembly includes a frequency generator and a cutting horn powered by the frequency generator. The cutting horn is spaced apart from the body so that the body is restricted from damping vibrational movement of the cutting horn. The dermatome assembly is operable to precisely control the thickness of the cut skin graft and also restrict the cutting horn from overheating.

40 Claims, 6 Drawing Sheets

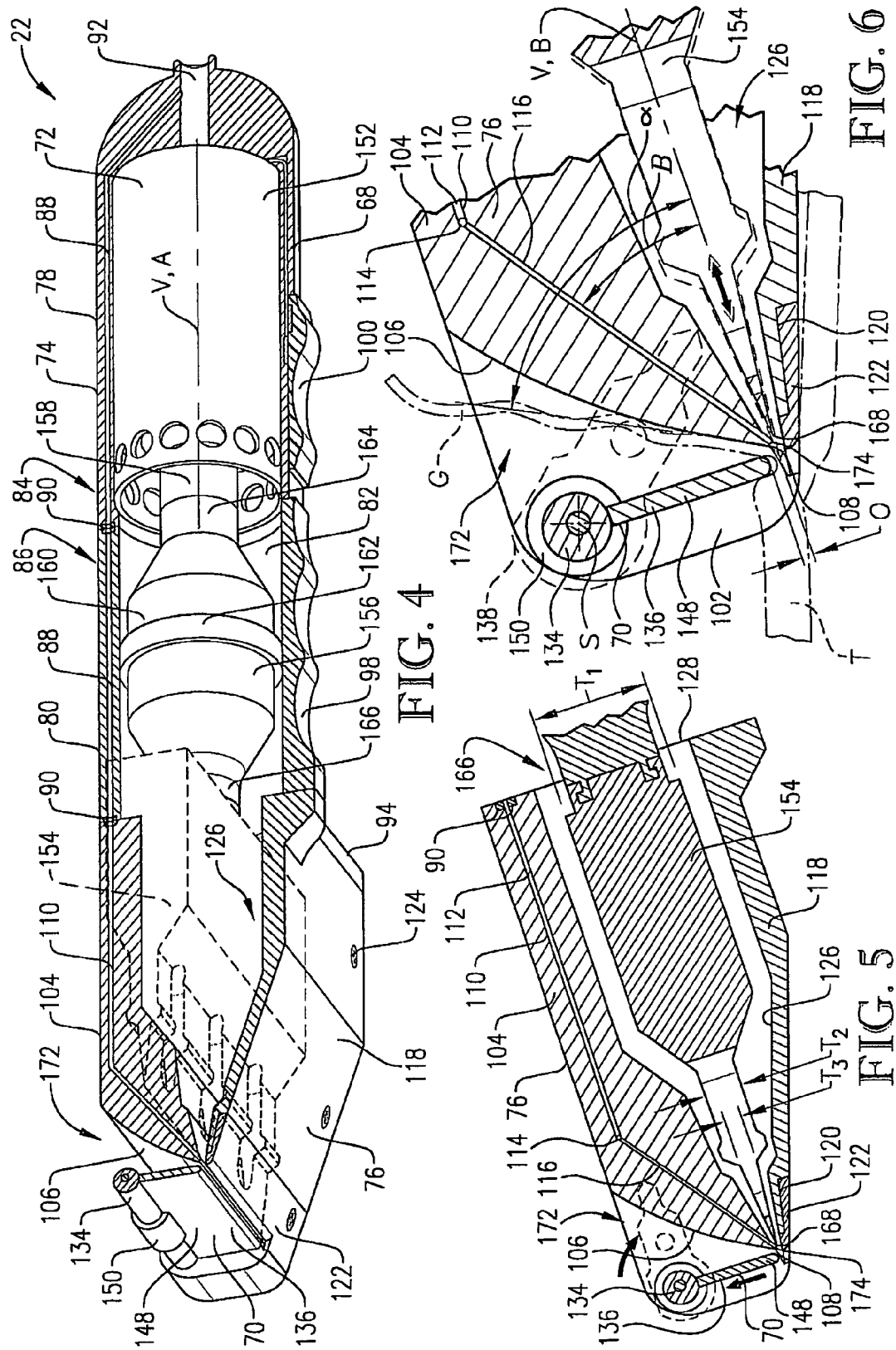

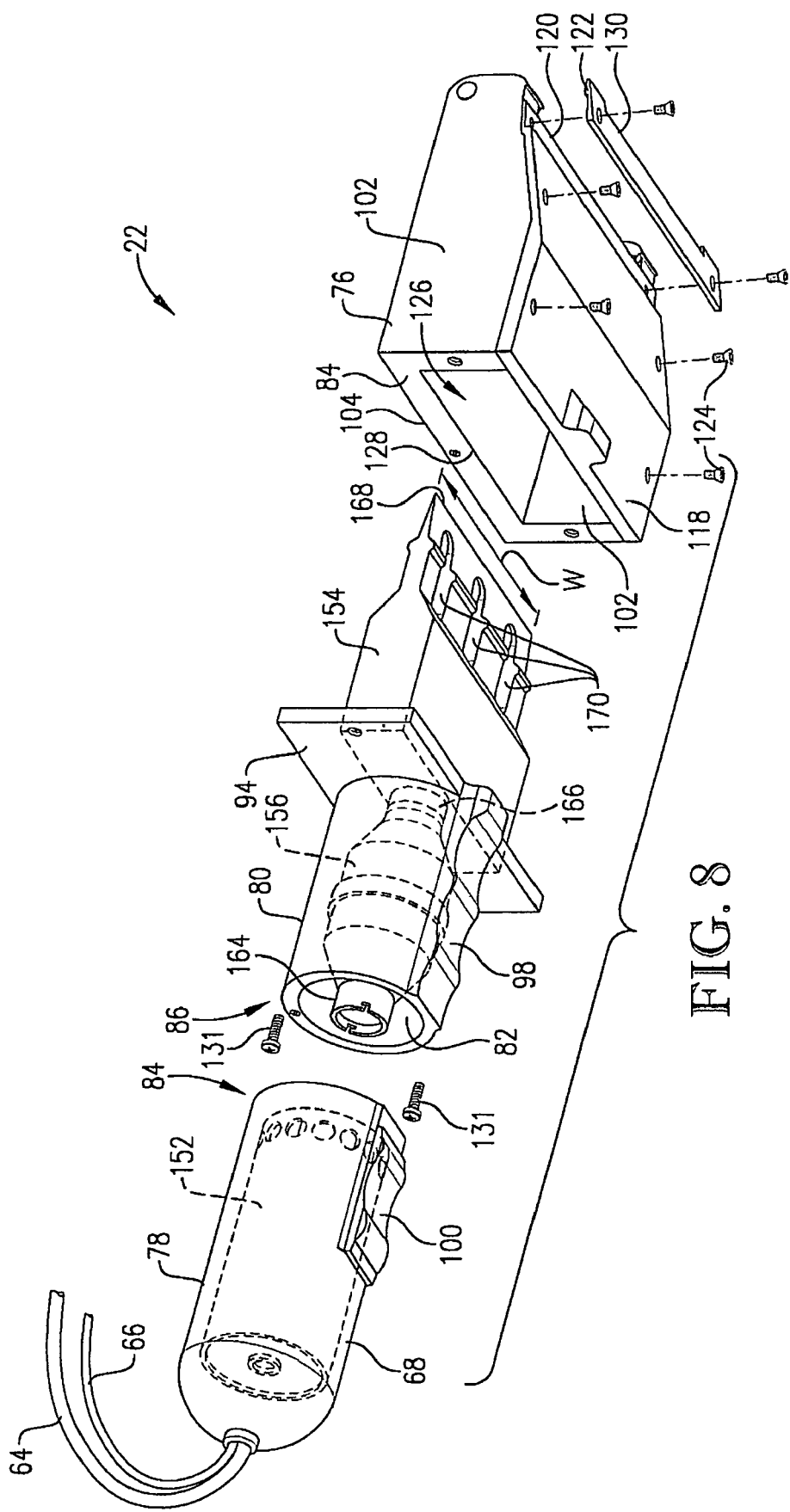

DERMATOME WITH ULTRASONIC CUTTING BLADE

RELATED APPLICATION

This application claims the benefit of U.S. Provisional Application No. 60/990,867, filed Nov. 28, 2007, entitled DERMATOME WITH ULTRASONIC CUTTING BLADE, which is hereby incorporated in its entirety by reference herein.

BACKGROUND

1. Field

The present invention relates generally to devices for harvesting skin grafts. More specifically, embodiments of the present invention concern an ultrasonic dermatome.

2. Discussion of Prior Art

A dermatome is a medical instrument for cutting skin grafts and has been in use since the early 1900s. Prior art dermatomes include a blade with a straight razor-like edge and a head that can be adjusted to vary the width and thickness of the skin graft. Conventional dermatomes are either manually operated or electrically powered. Powered dermatomes are generally able to cut skin grafts more easily and more precisely than manual dermatomes. One electrically powered dermatome includes a blade that is driven in a side-to-side oscillating motion along the length of the blade edge and is powered by an electric motor and a mechanical drive.

Prior art dermatomes have a number of undesirable limitations. For example, conventional dermatomes require significant physical effort and coordination to operate and typically require more than one person to perform the procedure of cutting a skin graft. In particular, conventional dermatomes require the user to apply a precise amount of pressure to the dermatome while precisely controlling the speed at which the dermatome is drawn along the skin. Powered dermatomes are also notorious for generating an excessive amount of mechanical noise. Furthermore, the mechanical drive of prior art powered dermatomes are prone to undesirable wear and failure after only 20-30 hours of continuous use.

SUMMARY

Embodiments of the present invention provide an ultrasonic dermatome that does not suffer from the problems and limitations of the prior art dermatomes set forth above.

A first aspect of the present invention concerns an ultrasonic dermatome broadly including a body, an ultrasonic frequency generator, a blade element, and a gauge bar. The body includes a handle. The ultrasonic frequency generator is mounted to the handle. The blade element presents proximal and distal ends. The blade element is drivingly attached to the frequency generator adjacent the proximal end and presents a cutting edge along the distal end, with the cutting edge being operable to cut a skin graft. The gauge bar is supported by the body and positioned adjacent the cutting edge to engage the skin. The gauge bar and cutting edge are spaced apart to present a graft opening through which the skin graft is operable to pass when cut. The blade element is supported by the body to define a distal cantilevered blade section that includes the cutting edge. The distal cantilevered blade section is spaced apart from the body to restrict the body from damping ultrasonic energy transmitted from the ultrasonic frequency generator to the cutting edge.

A second aspect of the present invention concerns an ultrasonic dermatome broadly include a body, an ultrasonic frequency generator, and a blade element. The body includes a handle. The ultrasonic frequency generator is mounted to the handle. The blade element presents proximal and distal ends. The blade element is drivingly attached to the frequency generator adjacent the proximal end and presents a cutting edge along the distal end, with the cutting edge being operable to cut a skin graft. The body presents a coolant channel that is fluidly connectable to a coolant source and extends through the handle and terminates at a channel outlet. The outlet is positioned adjacent the cutting edge, with the coolant channel being operable to supply coolant through the outlet and on the cutting edge while the skin graft is being cut.

A third aspect of the present invention concerns a method of harvesting a skin graft broadly including the step of cutting the skin graft with the cutting edge of an ultrasonic dermatome. The cutting step includes the steps of vibrating the cutting edge to cut the skin graft and simultaneously discharging coolant on the cutting edge.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 4 is a lower perspective of the ultrasonic dermatome shown in FIGS. 1 and 3, showing the body and gauge bar assembly of the ultrasonic dermatome cross-sectioned to show an ultrasonic blade of the ultrasonic dermatome, with the ultrasonic blade including a frequency generator, a booster, and a cutting horn drivingly interconnected, and with the cutting horn cantilevered from the booster;

Figure 1:
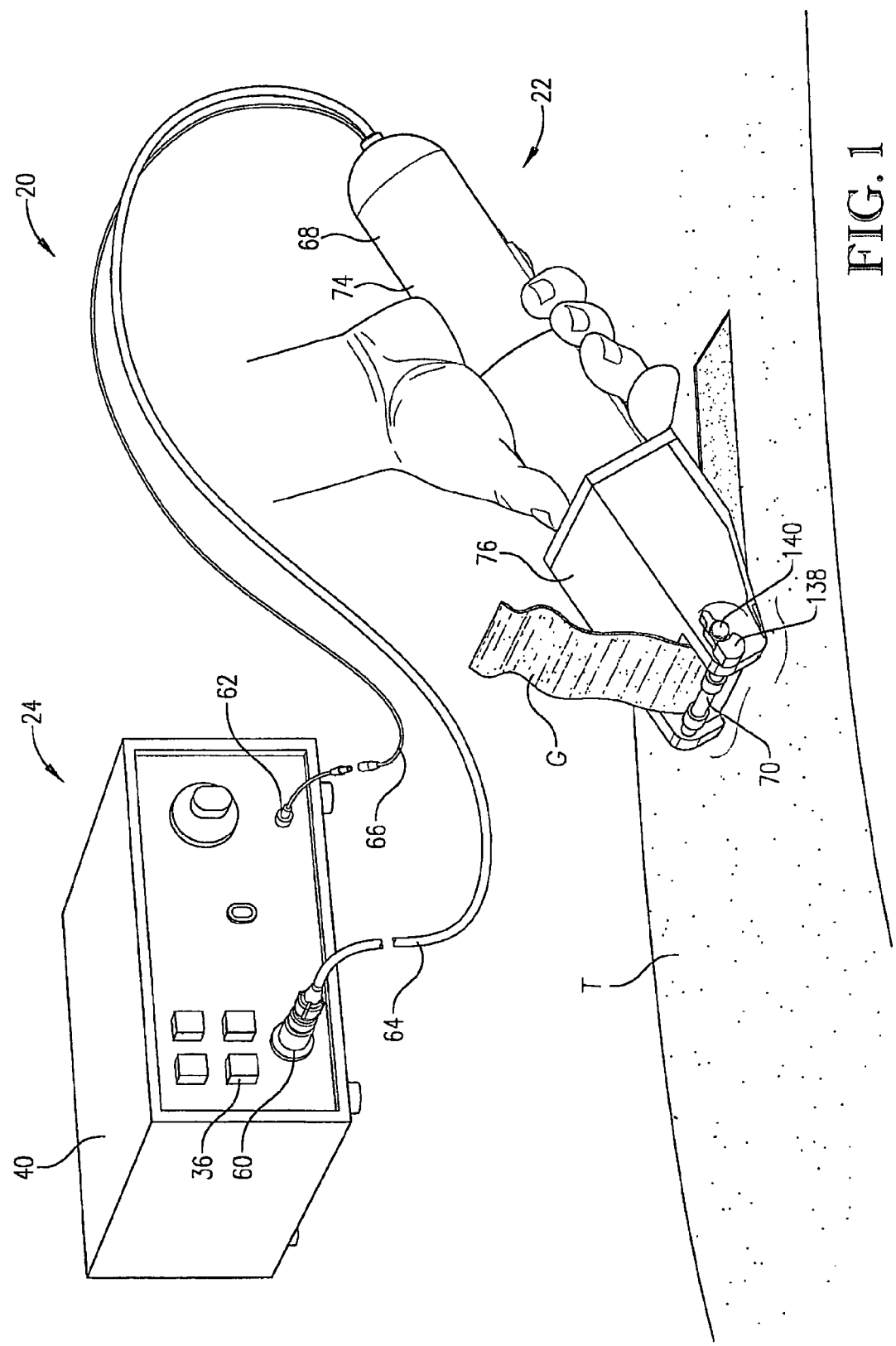
FIG. 1 is a perspective of a dermatome assembly constructed in accordance with a preferred embodiment of the present invention, with the dermatome assembly including an ultrasonic dermatome and a power supply connected by umbilical lines, and showing a skin graft being harvested from tissue.
Figure 3:
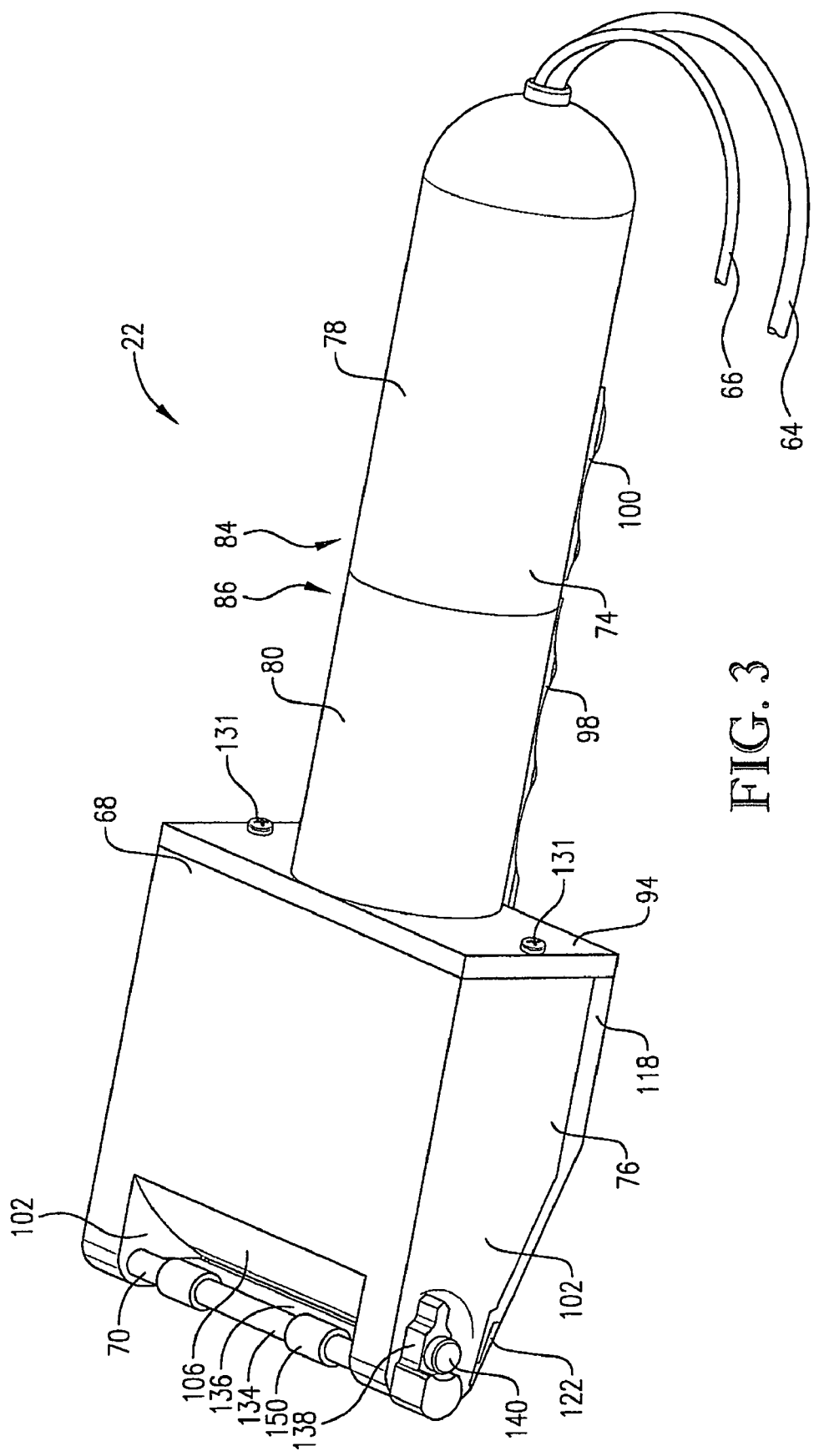
FIG. 3 is an upper perspective of the ultrasonic dermatome shown in FIG. 1, showing a body of the dermatome, including a handle, a head, and also showing a gauge bar assembly of the dermatome, with the umbilical lines extending from a proximal end of the handle.
Figure 7:
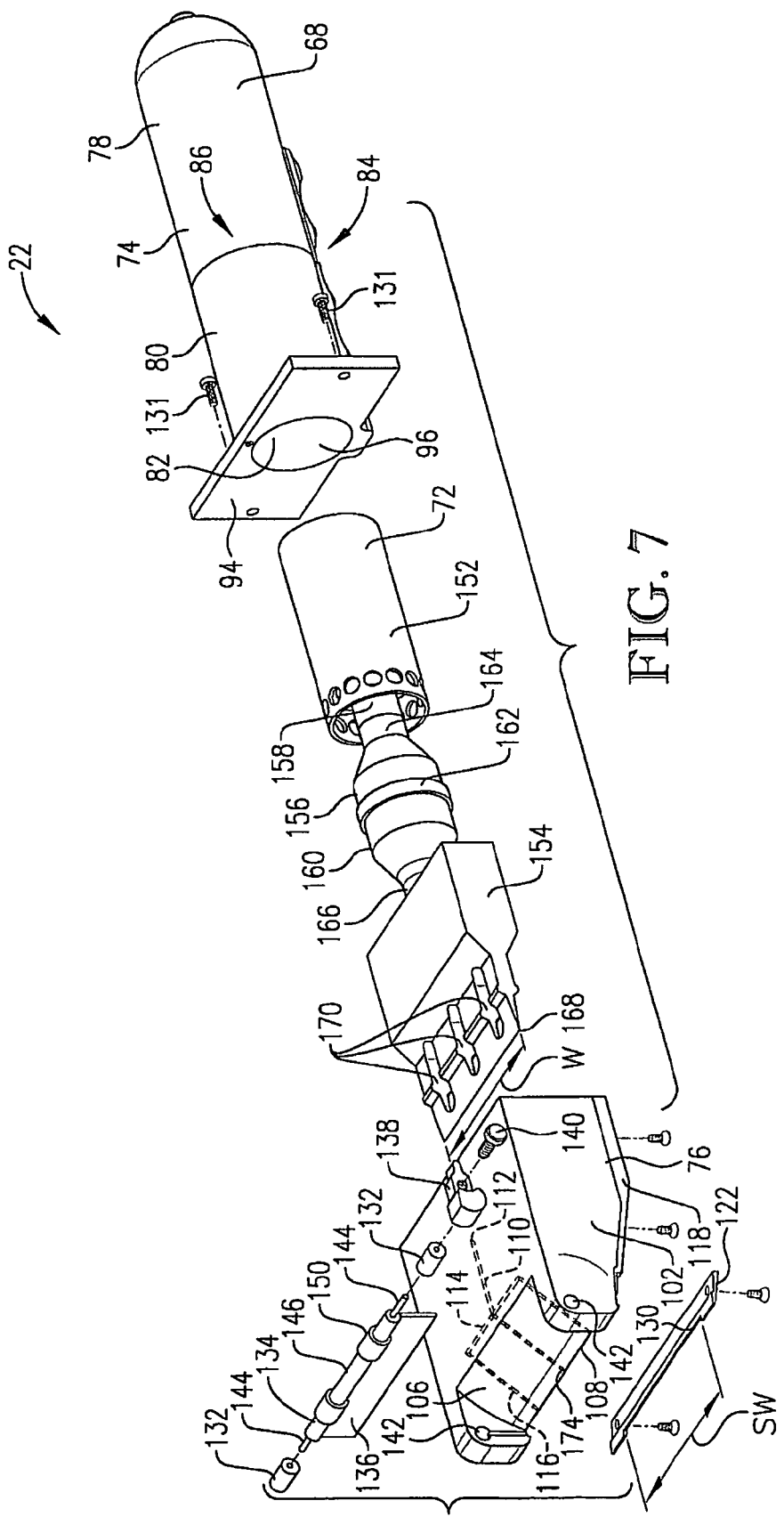

FIG. 5 is a fragmentary cross-section of the ultrasonic dermatome shown in FIGS. 1, 3, and 4, showing the head, the gauge bar assembly, and the cutting horn cantilevered within the head, with the head including an upper plate spaced above the cutting horn, a guide foot spaced below the cutting horn, and a blade cover attached to a distal end of the guide foot, and also showing a gauge bar of the gauge bar assembly in a lowermost position;

FIG. 6 is an enlarged fragmentary cross-section of the ultrasonic dermatome shown in FIGS. 1 and 3-5, showing vibrational movement of the cutting horn along a fore-and-aft vibrational axis, and showing the gauge bar in an uppermost position;

FIG. 7 is an exploded view of the ultrasonic dermatome shown in FIGS. 1 and 3-6, showing sections of the handle attached to each other and showing the handle removed from the head; and FIG. 8 is an exploded view of the ultrasonic dermatome shown in FIGS. 1 and 3-7, showing the handle section removed from one another and the booster and frequency generator separator so that the frequency generator and proximal handle section cooperatively form a frequency generator module of the dermatome and the remaining components of the dermatome form a cutting module.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Figure 2:
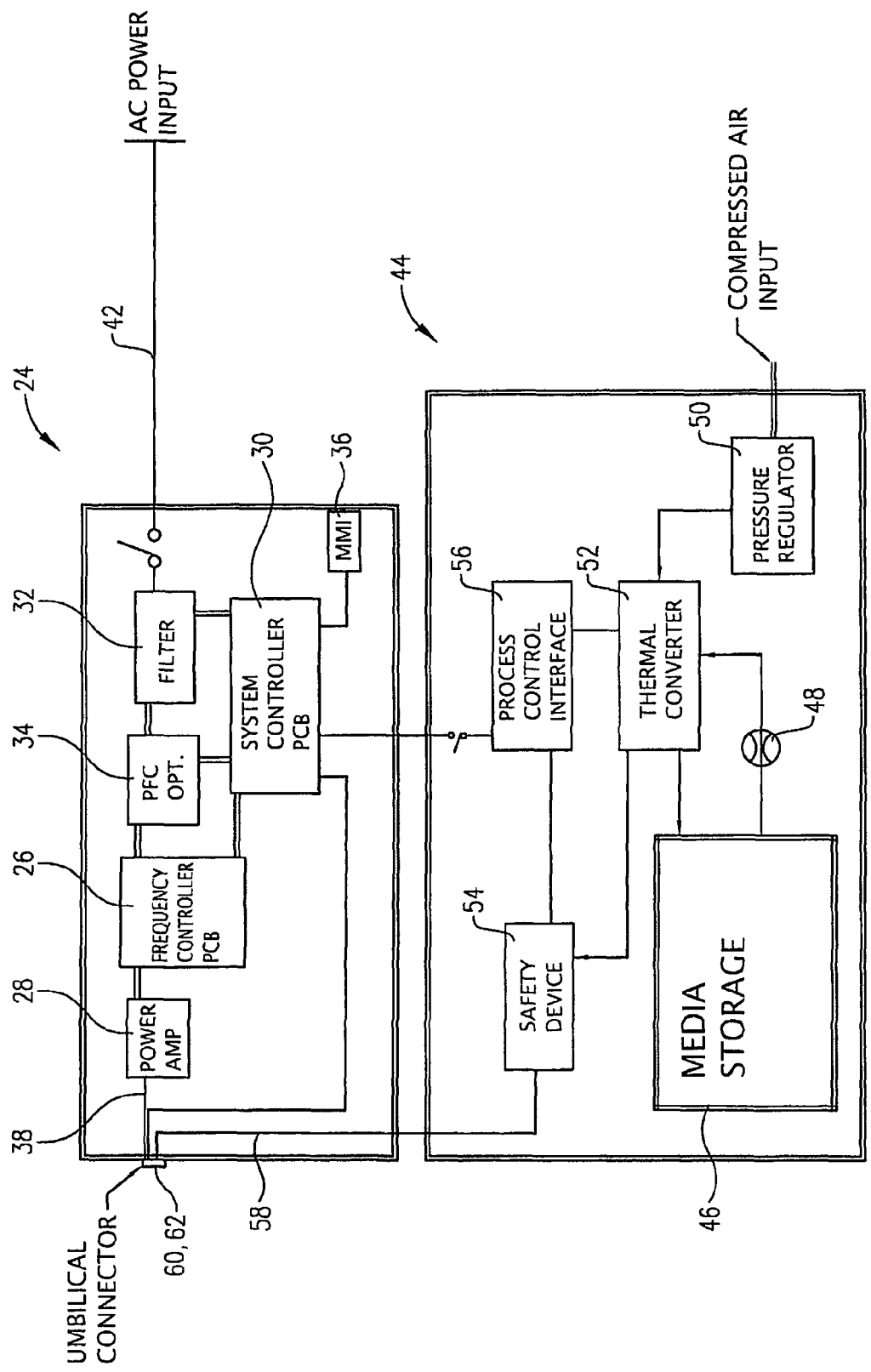
FIG. 2 is a schematic view of power supply shown in FIG. 1, showing various components of the power supply, including a coolant supply.

Turning initially to FIGS. 1 and 2, a dermatome assembly 20 is operable to remove a skin graft G from tissue T. The skin graft G removed by the dermatome assembly 20 is typically used in repairing an area of damaged skin, e.g., from burning, or for use in cosmetic surgery. The skin graft G may be harvested from tissue of a live patient or from a cadaver. The illustrated dermatome assembly 20 is particularly effective under extended use, e.g., for use at a skin bank where skin grafts can be harvested throughout the day. The dermatome assembly broadly includes an ultrasonic dermatome 22 and a power supply 24.

As will be discussed in greater detail, the power supply 24 drives the ultrasonic dermatome 22 and provides a supply of coolant. The power supply 24 broadly includes a frequency controller 26, a power amplifier 28, a system controller 30, a power filter 32, power factor correction 34, a power supply interface 36, a power output line 38, and a power supply housing 40. The power supply 24 also receives power via an A/C power input line 42. In the usual manner, the power supply 24 provides a power signal to the dermatome 22 via the power output line 38 and thereby controls the vibrational frequency and amplitude. For example, the power supply 24 can be adjusted by the user to control the vibrational amplitude. This adjustment is particularly helpful to provide efficient cutting operation as properties of the tissue T change and as the thickness of the skin graft G changes. The power supply 24 also is operable to automatically tune to the precise resonant frequency of the dermatome 22. The power supply 24 also includes an overload circuit to detect when the dermatome 22 encounters too much resistance, e.g., due to the tissue T, and automatically shuts off power to the dermatome 22. In this manner, the power supply 24 protects itself from damage and restricts heat buildup in the dermatome 22, particularly along the cutting edge. Furthermore, the interface 36 includes a warning light operably connected to the overload circuit and the warning light provides a visual indication to the user that the dermatome 22 is approaching an overload condition. Thus, the user can shut down the dermatome 22 prior to reaching overload.

The power supply 24 also includes a coolant supply 44 operable to cool the ultrasonic dermatome 22 during use, as will be discussed further. The coolant supply 44 preferably includes coolant container 46, a pump 48, a pressure regulator 50, a thermal converter 52, a safety valve 54, and a controller 56. The pump 48 draws coolant from the container 46 and circulates the coolant through the thermal converter 52, which acts as a heat exchanger and mixer to control coolant temperature. Some of the coolant is discharged through the valve 54 and into a coolant line 58, and some coolant is returned to the container 46.

The dermatome assembly 20 includes connectors 60,62 and umbilical lines 64,66 for interconnecting the dermatome 22 and the power supply 24. In particular, umbilical line 64 is connected to the power output line 38 by connector 60 and transmits power from the power supply 24 to the dermatome 22. Umbilical line 66 is fluidly connected to the coolant line 58 by connector 62 and transmits coolant from the coolant supply 44 to the dermatome 22.

The illustrated coolant supply 44 preferably contains and supplies a fluid coolant in the form of a conventional hepacleaner. However, the principles of the present invention are applicable where the coolant includes another type of liquid or includes a gas, such as air or an inert gas. For instance, the coolant could comprise a moist stream of air. While the illustrated coolant supply 44 is operable to cool the ultrasonic dermatome 22 by providing a supply of fluid coolant, it is also within the ambit of the present invention where the dermatome assembly 20 includes another mechanism for cooling the dermatome 22, such as thermoelectric cooling. For certain aspects of the present invention, the dermatome assembly 20 may not include a cooling mechanism.

The components of the power supply 24 are all preferably contained in the housing 40, but it is also within the ambit of the present invention where the power supply components are alternatively housed. For instance, the coolant supply 44 could be housed separately from the rest of the power supply 24. Also, at least some components of the power supply 24 could be housed in the ultrasonic dermatome 22.

Turning to FIGS. 3-8, the ultrasonic dermatome 22 is powered by the power supply 24 to harvest the skin graft G and broadly includes a body 68, a gauge bar assembly 70, and an ultrasonic blade assembly 72. As will be discussed further, the blade assembly 72 is operable to vibrate at ultrasonic frequencies for cutting of the skin graft G.

The illustrated body 68 broadly includes a handle 74 and head 76 that are removably attached to one another and cooperatively serve as a chassis for the ultrasonic dermatome 22. The handle 74 comprises an elongated tubular structure and includes a pair of proximal and distal handle sections 78,80 that are removably attached to one another and cooperatively present an internal chamber 82. In particular, the handle sections 78,80 include mating connector ends 84,86 that cooperatively provide a releasable fluid-transmitting joint for permitting access to the chamber 82. It is within the ambit of the present invention where the releasable mechanism that holds the ends 84,86 together comprises a conventional connector that includes threaded connectors or fasteners. The handle sections 78,80 each present coolant channels 88 that are fluidly connected to each other at the joint and are sealed by gaskets 90. As will be discussed, the handle sections 78,80 are separable to permit sterilization of the dermatome 22. However, it is also within the scope of the present invention where the releasably joint does not transmit coolant.

Handle section 78 presents a proximal opening 92 that receives the umbilical lines 64,66. Handle section 80 also includes a distal flange 94 operable to be attached the head 76, and the handle section 80 presents a distal opening 96 that permits access to the chamber 82. The handle 74 also includes a contoured grip 98 attached to the handle section 80 and a movable switch 100 slidably attached to the handle section 78. The handle 74 is preferably manufactured from a metallic material, such as stainless steel, but could include other materials suitable for medical devices, such as plastics.

The head 76 presents proximal and distal head ends and includes side walls 102 that extend between the ends. The side walls 102 present upper and lower margins and are interconnected by an upper plate 104. The upper plate 104 extends between the proximal and distal head ends. The upper plate 104 includes a proximal section that is attached to the side walls along the upper margins and a distal section that extends toward the lower margins of the side walls 102. As will be discussed, the distal section serves to direct the skin graft G and presents a separator surface 106 that extends in a proximal direction from a distal separator edge 108. The upper plate 104 also includes an internal coolant channel 110 that includes a supply portion 112, a lateral manifold portion 114, and three angled portions 116 that fluidly communicate with the manifold portion 114 and extend to outlets adjacent the distal separator edge 108. As will be discussed the coolant channel 110 is operable to discharge coolant for cutting the skin graft G.

The head 62 also includes a removable lower guide foot 118 that presents a transversely extending distal groove 120, and a removable blade cover 122 received by the distal groove 120. The lower guide foot 118 is attached to the side walls 102 with fasteners 124, and is positioned so that the distal groove 120 is positioned adjacent the distal separator edge 108. The side walls 102, upper plate 104, and guide foot 118 cooperatively present a head chamber 126 and a proximal opening 128 (see FIG. 8) that permits access to the head chamber 126. The head chamber 126 presents a thickness that tapers toward a distal end of the head 76, and a width that is substantially constant between the distal and proximal ends of the head 76. The head chamber 126 is operable to receive the blade assembly 72, with the blade assembly 72 extending into and out of the chamber 126 via the proximal opening 128.

The blade cover 122 is unitary and includes opposite ends and a laterally extending distal slot 130 that presents a slot width SW (see FIG. 7). As will be discussed further, the distal slot 130 defines an effective blade width of the dermatome 22. The head 62 is attached to the handle 74 with threaded fasteners 131 that extend through holes in the flange 94 and into the side walls 102. Furthermore, the head 62 and handle 74 are attached so that channels 88 fluidly communicate with channel 110, with the channels 88,110 being sealed by gaskets 90. Thus, the head 62 and handle 74 cooperatively form the body 68, with a longitudinal body axis A. The illustrated body 68 preferably has a length less than about 12 inches, but could be longer than 12 inches without departing from the scope of the present invention.

Turning to FIGS. 3-7, the gauge bar assembly 70 cooperates with the blade assembly 72 to determine the thickness of the skin graft G. The gauge bar assembly 70 preferably includes a pair of bushings 132, an eccentric shaft 134, a gauge bar 136 pivotally mounted on the shaft 134, an adjustment knob 138, and a locking fastener 140 (see FIG. 7). Each side wall 102 presents a lateral bore 142 positioned adjacent the distal head end and adjacent the upper margin. The bores 142 are coaxial and each are configured to receive a corresponding bushing 132 therein.

The eccentric shaft 134 presents opposite shaft ends 144 that define a shaft axis S, and a central cam 146 that interconnects the shaft ends 144 and presents a cylindrical cam surface that is axially offset from the shaft axis S. The eccentric shaft 134 is rotatably mounted on the head by inserting each shaft end 144 into a corresponding bushing 132.

The gauge bar 136 includes a rectangular gauge plate 148 that presents upper and lower margins. The gauge bar 136 also includes a pair of sleeves 150 fixed to the gauge plate 148 along the upper margin, with the sleeves 150 presenting a common axis. The gauge bar 136 is rotatably mounted on the eccentric shaft 134 by extending the central cam 146 through the sleeves 150. The gauge bar 136 also includes opposite ends slidably mounted in slots presented by the side walls 102. As the shaft 134 is rotated about the shaft axis S, the sleeves follow the axis of the cylindrical cam surface. Thus, rotational movement of the shaft 134 causes up-and-down movement of the gauge bar 136 within the slots of the side walls 102.

The adjustment knob 138 is attached to one of the shaft ends 144, with pivotal movement of the knob 138 causing the shaft 134 to rotate in the same direction. The locking fastener 140 comprises a fastener that is threaded into the knob 138 and can be adjusted into and out of engagement with the corresponding side wall 102. Thus, the fastener 140 is operable to selectively lock the adjustment knob 138 into a position to restrict up-and-down movement of the gauge bar 136. While the illustrated gauge bar assembly 70 is preferable, it is also within the scope of the present invention where the gauge bar assembly 70 is alternatively constructed to engage the skin graft G and to cooperate with the blade assembly 72 to control the thickness of the skin graft G.

Turning to FIGS. 4, 7, and 8, the ultrasonic blade assembly 72 is operable to vibrate at a resonant frequency and broadly includes a frequency generator 152, a cutting horn 154, and a booster 156 that interconnects the frequency generator 152 and horn 154. The frequency generator 152 preferably comprises a piezoelectric transducer that is operable to vibrate an output end 158 in an in-line direction along a vibration axis V at a frequency of at least about 10 kHz. More preferably, the generator 152 vibrates at a frequency between about 20 kHz and about 70 kHz during normal operation. Most preferably, the generator 152 vibrates at a frequency between about 30 kHz and about 40 kHz. It is also within the ambit of the present invention where the generator 152 is another transducer that converts an electrical signal into vibrational movement, such as a magnetostrictive transducer. The generator 152 is operably coupled to the switch 100 so that the generator 152 can be turned on and off by the switch 100.

In the usual manner, the booster 156 is operable to tune the blade assembly to a resonant frequency and includes a tuned booster section 160 and a sleeve 162. The booster section 160 includes opposite proximal and distal ends 164,166 and a central portion that presents a maximum diameter of the booster section 160, with the central portion tapering toward each end 164,166. The sleeve 162 extends around the central portion and supports the booster 156 within the handle 74. The booster 156 is removably attached to the frequency generator 152. In particular, the proximal end 164 and the output end 158 include mating connectors. While the illustrated connectors comprise a bayonet-type connector assembly, the principles of the present invention are applicable where other types of connectors are used to mount the booster 156 to the frequency generator 152.

Turning to FIGS. 4-8, the cutting horn 154 comprises a blade with proximal and distal ends and a blade axis B that extends between the ends. The blade presents a distal cutting edge 168 perpendicular to the blade axis B, and the distal cutting edge 168 has a blade edge width W. The blade edge width W is preferably at least about one-half inch. More preferably, the cutting horn 154 can be provided with a blade edge width W between about one inch and about six inches. The cutting horn 154 presents a longitudinal cross section that tapers from the proximal end toward the distal cutting edge 168 (see FIG. 5). In particular, the blade includes a proximal section that tapers from a first thickness T1 to a second thickness T2, an intermediate section that tapers from the second thickness T2 to a third thickness T3, and a distal section that tapers from the third thickness T3 to the cutting edge 148. Preferably, thickness T2 is about one-third of thickness T1 and thickness T3 is about one-half of thickness T2. However, the principles of the present invention are applicable where the cutting horn 154 presents alternative shapes and dimensions. The blade also preferably includes three slotted openings 170 that extend between the distal and intermediate sections (see FIG. 7). The illustrated openings 170 are elongated and each present a longitudinal axis parallel to the blade axis B. The illustrated openings 170 are also spaced side-by-side and are spaced apart from each other and from the cutting edge 168. In this manner, the openings 170 direct vibrational energy along the blade axis B and restrict vibrational energy from traveling in a lateral direction relative to the blade axis B. It is within the scope of the present invention where the cutting horn 154 includes an alternative number or configuration of the openings 170. The illustrated cutting horn 154 is preferably made of a titanium alloy, but could include other materials, such as stainless steel.

The cutting horn 154 is removably attached to the booster 156. In particular, the distal end 166 and the proximal end of the cutting horn 154 include mating connectors. While the illustrated mating connectors comprise a bayonet-type connector assembly, the principles of the present invention are applicable where other types of connectors are used to mount the booster 156 to the cutting horn 154.

The cutting horn 154 and booster 156 cooperatively provide a blade assembly that preferably vibrates along the vibration axis V, and the blade axis B is preferably parallel to the vibration axis V. However, it is also within the scope of the present invention where the blade axis and vibration axis V are perpendicular to each other or present an oblique angle therebetween. The illustrated blade assembly preferably vibrates at a resonant frequency of at least about 10 kHz. More preferably, the blade assembly has a resonant frequency between about 20 kHz and about 70 kHz. Most preferably, the resonant frequency is between about 30 kHz and about 40 kHz. The illustrated cutting edge 168 is preferably perpendicular to the vibration axis V.

The frequency generator 152 is mounted within the proximal handle section 78, with the output end 158 projecting distally. Furthermore, the booster 156 is mounted within the distal handle section 80 and is supported therein by the sleeve 162. However, the principles of the present invention are applicable where the booster 156 is spaced apart from and is unsupported by the handle 74. The cutting horn 154 is spaced within the chamber 82 and is entirely spaced apart from the gauge bar assembly 70 and body 68. Thus, the cutting horn 154 is cantilevered from booster 156.

The blade assembly 72 is positioned with the cutting edge 168 adjacent the slot 130 of the blade cover 122. The blade cover 122 is arranged to permit the cutting edge 168 to cut the tissue T only along the width of the slot 130. The illustrated slot width SW is about the same as the blade edge width W, with the slot 130 and cutting edge 168 being substantially coextensive with one another. However, it is also within the ambit of the present invention where the blade edge width W is greater than the slot width SW and the blade cover 122 only permits cutting of tissue T along the slot width SW. In this manner, multiple blade covers having slots 130 of different widths can be used with the same cutting horn 154 to provide different effective blade widths of the dermatome 22, with each cover thereby cooperating with the cutting horn 154 to harvest skin grafts with a corresponding skin graft width. In other words, the blade edge width W defines the maximum width of the skin graft G.

The illustrated dermatome 22 has a modular construction and is configured to be sterilized using conventional autoclave equipment without damaging the frequency generator 152. Conventional frequency generators can be damaged by temperatures above 140° F., and autoclaves used to sterilize medical equipment traditionally exceed this temperature limit. Consequently, the dermatome 22 is operable to be quickly separated for sterilization. In particular, the handle sections 78,80 can be separated from one another, and the booster 156 can be separated from the frequency generator 152 (see FIG. 8). Thus, the booster 156 and frequency generator 152 comprise a frequency generator module of the dermatome 22 that can be sterilized at temperatures below 140° F., e.g., by using ethylene oxide or ozone. The remainder of the dermatome 22 comprises a cutting module that can be sterilized using a conventional autoclave at temperatures above 140° F. The modular dermatome construction also permits quick replacement of the frequency generator 152 and cutting horn 154.

Turning again to FIGS. 4-8, the blade assembly 72 is operably mounted within the body 68 to define a dermatome cutting direction along the blade axis B and vibration axis V, with the cutting direction being normal to the cutting edge 168. The blade assembly 72 is mounted within the body 68 so that the cutting direction is preferably away from the handle 74 and along the body axis A. However, it is also within the ambit of the present invention where the cutting direction is toward the handle 74 along the body axis A, or is in a direction not aligned with the body axis A, e.g., perpendicular to the body axis A. Furthermore, the blade assembly 72 is mounted so that the body axis A and vibration axis V are parallel, but the axes A and V could be perpendicular or arranged in a non-parallel configuration without departing from the scope of the present invention.

The blade assembly 72 is also supported within the body 68 so that vibration transmitted from the generator 152 to the cutting edge 168 is minimally damped. In particular, the cutting horn 154 is cantilevered from booster 156 so that the body 68 and gauge bar assembly 70 are restricted from touching and thereby damping vibrational movement of the cutting horn 154. Furthermore, the booster 156 is supported by the handle 74 at a location along the vibrational axis V where such support will cause minimal damping. It has been found that the blade assembly 72 vibrating at a resonant frequency will have at least one dead area or node along the vibrational axis V where the essentially no displacement along the axis V occurs. This dead area provides a preferred location for laterally supporting the blade assembly 72. The illustrated booster 156 preferably extends along the dead area for the blade assembly 72 and is supported along the dead area. Again, it is also within the ambit of the present invention for the booster 156 to be entirely spaced from the body 68. Furthermore, the blade assembly 72 could be entirely devoid of a booster 156 where the cutting horn is properly tuned to resonate at the desired frequency. Vibrational energy transmitted from the generator 152 causes the cutting edge 168 to move in an inline direction along the axis V (see FIG. 6). During vibrational movement, the cutting edge 168 preferably moves fore-and-aft through a total distance of less than about 0.010 inches.

Turning to FIGS. 4-6, the gauge bar 136 and cutting edge 168 cooperatively define a graft opening that receives the skin graft G as the skin graft G is cut and thereby determines the thickness of the skin graft. The illustrated gauge bar 136 is adjustable by movement of the knob 138 to shift up and down relative to the cutting edge 168 between a lowermost position (see FIG. 5) and an uppermost position (see FIG. 6). Preferably, the illustrated gauge bar 136 is operable to be spaced relative to the cutting edge 168 so that the graft opening presents an opening thickness O between about zero inches and about 0.040 inches. More preferably, the opening thickness O is operable to range from about 0.002 inches to about 0.030 inches.

The cutting edge 168 is also positioned immediately adjacent the distal separator edge 108, with the distal separator edge 108 being spaced above the cutting edge 168. Preferably, the cutting edge 168 is spaced from the distal separator edge 108 a distance less than about 0.100 inches. Thus, the distal separator edge 108 is operable to engage the cut skin graft G quickly after being cut from the tissue T and divert the skin graft G onto the separator surface 106.

The separator surface 106 is spaced proximally from the gauge bar 136, with the separator surface 106 and gauge bar 136 cooperatively presenting an open space 172 therebetween to receive the cut skin graft G as it moves past the cutting edge 168. Furthermore, the separator surface 106 is configured to carry the cut skin graft G away from the cutting horn 154. In particular, a distal portion of the separator surface 106 extends proximally from the distal separator edge 108 at a separation angle $\alpha$ measured relative to the blade axis B. Preferably, the separation angle $\alpha$ is at least about 20 degrees. More preferably, the separation angle $\alpha$ is in the range from about 30 degrees to about 60 degrees and, most preferably, is about 45 degrees. The illustrated separator surface 106 also preferably presents a convex shape so that the skin graft G can feed smoothly through the open space 172 and out of the head 76.

The coolant channel 110 is configured to receive coolant from the channels 88 and provide coolant directly to the cutting edge 168. The angled portions 116 of the coolant channel 110 each extend to a corresponding outlet 174. The outlets 174 are positioned immediately adjacent and just proximal of the distal separator edge 108. Furthermore, the angled portions 116 preferably extend between the separator surface 106 and the cutting horn 154, with the outlets 174 just above the cutting horn 154. However, the principles of the present invention are equally applicable where the angled portions 116 and outlets 174 are positioned below the cutting horn 154, e.g., by extending through the lower guide foot 118. It has been determined that the stream of coolant provided by the illustrated coolant channel 110 is operable to sufficiently cool the cutting horn 154, particularly along the cutting edge 168, to restrict damage (e.g., cauterization) of the tissue T and the skin graft G. Furthermore, the coolant flow is operable to cool the space between the cutting edge 168, the tissue T, and the skin graft G. It has also been unexpectedly determined that this cooling configuration is operable to reduce the heat generated by ultrasonic cutting (e.g., by fluid cavitation and friction between the cutting horn 154 and tissue T). Furthermore, this coolant flow can reduce friction between the skin graft G and components of the dermatome 22. While the illustrated cooling device is preferable, for some aspects of the present invention, another cooling mechanism could be used, such as a thermoelectric cooling.

The illustrated coolant channel 110 is also shaped and positioned to urge the skin graft G out of engagement with the cutting horn 154 and into the open space 172. The illustrated angle portions 116 extend proximally from the outlets 174 to present a channel angle $\beta$ relative to the blade axis B. Preferably, the channel angle $\beta$ is less than the separation angle $\alpha$. In this manner, the coolant flow out of the outlets 174 is operable to direct the skin graft out of a direction along the blade axis B and into the open space 172. Furthermore, this configuration permits coolant to flow into contact with the cutting edge 168 while allowing the coolant channel 110 to extend through the upper plate 104. However, the principles of the present invention are equally applicable where the channel angle $\beta$ is greater than the separation angle $\alpha$. For example, the angled portions 116 could extend through the lower guide foot 118 below the cutting horn 154 and be directed upwardly, perhaps even perpendicular to the blade axis B, toward the cutting edge 168 so that cutting fluid would flow in an upward direction and thereby direct the skin graft G upwardly into the open space.

In operation, the dermatome assembly 20 is turned on by moving the switch 100 to power the dermatome 22, which causes the frequency generator 152 to vibrate the cutting horn 154. Furthermore, coolant is simultaneously pumped by the coolant supply 44 via the umbilical line 66 into the channels 88,110 and through the outlets 174 onto the cutting edge 168. As the dermatome 22 is moved in the cutting direction across tissue T, the cutting edge 168 cuts the skin graft G by vibrating in the fore-and-aft direction. Simultaneously, coolant is discharged through the outlets 174 onto the cutting edge 168. In particular, the coolant is discharged along the cutting direction to contact the cutting edge 168 and impinge on the skin graft G and thereby direct the skin graft G upwardly away from the cutting horn 154 and into the open space 172. Thus, the cut skin graft G is separated from the cutting horn 154 by the separator surface 106 engaging the skin graft G and by the coolant flow engaging the cut skin graft G to deflect the skin graft G onto the separator surface 106. As the dermatome 22 continues over tissue T, the cut skin graft G becomes longer and the separator surface 106 guides the skin graft G through the open space 172 and out of the head 76. After the skin graft G is cut, the dermatome 22 can be sterilized by separating the frequency generator module from the cutting module. After sterilization, the dermatome 22 can be reassembled for further use.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An ultrasonic dermatome comprising:
    a body including a handle;
    an ultrasonic frequency generator mounted to the handle;
    a blade assembly drivingly coupled to the frequency generator so as to be selectively resonated at a natural frequency,
    said blade assembly including a blade element presenting proximal and distal ends,
    said blade element presenting a cutting edge along the distal end, with the cutting edge being operable to cut a skin graft; and
    a gauge bar supported by the body and positioned adjacent the cutting edge to engage the skin,
    said gauge bar and cutting edge being spaced apart to present a graft opening through which the skin graft is operable to pass when cut,
    said blade assembly being supported by the body to define a distal cantilevered blade section that includes the cutting edge, with any supporting contact between the blade assembly and body being generally at a node,
    said distal cantilevered blade section being spaced apart from the body and the gauge bar to restrict the body and the gauge bar from touching the blade section and thereby restrict damping ultrasonic energy transmitted from the ultrasonic frequency generator to the cutting edge.

2. The ultrasonic dermatome as claimed in claim 1,
said cutting edge comprising a substantially straight uninterrupted edge that defines a cutting direction normal to the edge.

3. The ultrasonic dermatome as claimed in claim 2,
said blade element presenting a longitudinal vibration axis extending between the proximal and distal ends,
said cutting edge extending in a lateral direction relative to the vibration axis.

4. The ultrasonic dermatome as claimed in claim 3,
said cutting edge being positioned transversely relative to the longitudinal vibration axis, with the cutting direction being along the longitudinal vibration axis.

5. The ultrasonic dermatome as claimed in claim 2,
said cutting edge presenting an edge width dimension measured transversely to the cutting direction and operable to define the maximum width of the skin graft,
said edge width dimension being at least about one-half inch.

6. The ultrasonic dermatome as claimed in claim 5,
said edge width dimension being between about one inch and about six inches.

7. The ultrasonic dermatome as claimed in claim 5,
said body including a blade cover that partly covers the cutting edge and presents a cover opening defining an effective blade width dimension about the same as the edge width dimension.

8. The ultrasonic dermatome as claimed in claim 1,
said blade assembly including a proximal booster section adjacent the proximal end of the blade element and drivingly interconnecting the blade element and frequency generator,
said booster section being operable to tune the resonant frequency.

9. The ultrasonic dermatome as claimed in claim 8,
said blade section presenting a blade thickness that tapers in a distal direction.

10. The ultrasonic dermatome as claimed in claim 9,
said blade section presenting a plurality of tapered segments that define the blade thickness and each taper in the distal direction.

11. The ultrasonic dermatome as claimed in claim 9,
said blade section including a longitudinal slotted opening spaced proximally from the cutting edge and operable to restrict ultrasonic energy from traveling laterally.

12. The ultrasonic dermatome as claimed in claim 8,
said blade element and booster section cooperatively having a resonant frequency between about 30 kHz and about 40 kHz.

13. The ultrasonic dermatome as claimed in claim 1,
said body including a head attached to the handle, with the head operably receiving the blade element therein,
said head supporting the gauge bar.

14. The ultrasonic dermatome as claimed in claim 13,
said gauge bar being shiftably mounted on the head to permit selective adjustment of an opening thickness dimension of the graft opening.

15. The ultrasonic dermatome as claimed in claim 14,
said opening thickness dimension being between about zero inches and about 0.040 inches.

16. The ultrasonic dermatome as claimed in claim 1,
said body including a head attached to the handle, with the head operably receiving the blade element therein,
said head including a graft separator section that presents an angled separator surface that tapers in a cutting direction to a distal separator edge extending along the cutting edge and positioned immediately adjacent thereto, with the separator section operable to direct the cut skin graft out of engagement with the cutting edge.

17. The ultrasonic dermatome as claimed in claim 16,
said head supporting the gauge bar,
said separator section spaced between the blade element and gauge bar and operable to direct the cut skin graft into a space between the separator section and gauge bar.

18. The ultrasonic dermatome as claimed in claim 16,
said blade section presenting a blade section axis extending transversely to the cutting edge,
said angled separator surface extending proximally from the distal separator edge at an oblique angle relative to the blade section axis of about 45 degrees.

19. The ultrasonic dermatome as claimed in claim 16,
said distal separator edge being spaced from the cutting edge a distance of less than about 0.100 inches.

20. The ultrasonic dermatome as claimed in claim 1,
said body including a head attached to the handle, with the head operably receiving the blade element therein,
said handle including a pair of hollow handle sections, with one section spaced between the other section and the head,
said other section receiving the ultrasonic frequency generator therein,
said handle sections being removably attached to one another so that the one section and head can be removed from the other section and ultrasonic frequency generator for sterilization.

21. The ultrasonic dermatome as claimed in claim 1,
said blade assembly further including a proximal booster section drivingly connected between the blade element and ultrasonic frequency generator,
said handle including a wall that extends axially along and is in supporting contact with the booster section, with the booster section being operable to transmit ultrasonic energy between the ultrasonic frequency generator and the blade section and tune the resonant frequency.

22. An ultrasonic dermatome comprising:
a body including a handle;
an ultrasonic frequency generator mounted to the handle; and
a blade assembly drivingly coupled to the frequency generator so as to be selectively resonated at a natural frequency,
said blade assembly including a blade element presenting proximal and distal ends,
said blade element presenting a cutting edge along the distal end, with the cutting edge being operable to cut a skin graft,
said blade assembly being supported by the body to define a distal cantilevered blade section that includes the cutting edge, with any supporting contact between the blade assembly and body being generally at a node,
said body including a graft separator section presenting an angled separator surface that tapers in a cutting direction to a distal separator edge extending along the cutting edge and positioned immediately adjacent thereto, with the separator section operable to direct the cut skin graft out of engagement with the cutting edge,
said distal cantilevered blade section being spaced apart from the separator section to restrict the separator section from touching the blade section and thereby restrict damping ultrasonic energy transmitted from the ultrasonic frequency generator to the cutting edge.

23. The ultrasonic dermatome as claimed in claim 22,
said cutting direction being generally normal to the cutting edge.

24. The ultrasonic dermatome as claimed in claim 23,
said blade element presenting a longitudinal vibration axis extending between the proximal and distal ends,
said cutting edge extending in a lateral direction relative to the vibration axis.

25. The ultrasonic dermatome as claimed in claim 24,
said cutting edge being positioned transversely relative to the longitudinal vibration axis, with the cutting direction being along the longitudinal vibration axis.

26. The ultrasonic dermatome as claimed in claim 23,
said cutting edge presenting an edge width dimension measured transversely to the cutting direction and operable to define the maximum width of the skin graft,
said edge width dimension being at least about one-half inch.

27. The ultrasonic dermatome as claimed in claim 26,
said edge width dimension being between about one inch and about six inches.

28. The ultrasonic dermatome as claimed in claim 26,
said body including a blade cover that partly covers the cutting edge and presents a cover opening defining an effective blade width dimension about the same as the edge width dimension.

29. The ultrasonic dermatome as claimed in claim 22,
said blade assembly including a proximal booster section adjacent the proximal end of the blade element and drivingly interconnecting the blade element and frequency generator,
said booster section being operable to tune the resonant frequency.

30. The ultrasonic dermatome as claimed in claim 29,
said blade section presenting a blade thickness that tapers in a distal direction.

31. The ultrasonic dermatome as claimed in claim 30,
said blade section presenting a plurality of tapered segments that define the blade thickness and each taper in the distal direction.

32. The ultrasonic dermatome as claimed in claim 30,
said blade section including a longitudinal slotted opening spaced proximally from the cutting edge and operable to restrict ultrasonic energy from traveling laterally.

33. The ultrasonic dermatome as claimed in claim 29,
said blade element and booster section cooperatively having a resonant frequency between about 30 kHz and about 40 kHz.

34. The ultrasonic dermatome as claimed in claim 22,
said body including a head attached to the handle, with the head operably receiving the blade element therein; and
a gauge bar supported by the body and positioned adjacent the cutting edge to engage the skin,
said gauge bar and cutting edge being spaced apart to present a graft opening through which the skin graft is operable to pass when cut,
said head supporting the gauge bar.

35. The ultrasonic dermatome as claimed in claim 34,
said blade element being supported by the body to define a distal cantilevered blade section that includes the cutting edge,
said distal cantilevered blade section being spaced apart from the body and the gauge bar to restrict the body and the gauge bar from touching the blade section and thereby restrict damping ultrasonic energy transmitted from the ultrasonic frequency generator to the cutting edge.

36. The ultrasonic dermatome as claimed in claim 22,
said body including a head attached to the handle, with the head operably receiving the blade element therein; and
a gauge bar supported by the body and positioned adjacent the cutting edge to engage the skin,
said gauge bar and cutting edge being spaced apart to present a graft opening through which the skin graft is operable to pass when cut,
said head supporting the gauge bar,
said graft separator section spaced between the blade element and gauge bar and operable to direct the cut skin graft into a space between the separator section and gauge bar.

37. The ultrasonic dermatome as claimed in claim 22,
said blade section presenting a blade section axis extending transversely to the cutting edge,
said angled separator surface extending proximally from the distal separator edge at an oblique angle relative to the blade section axis of about 45 degrees.

38. The ultrasonic dermatome as claimed in claim 22,
said distal separator edge being spaced from the cutting edge a distance of less than about 0.100 inches.

39. The ultrasonic dermatome as claimed in claim 22,
said body including a head attached to the handle, with the head operably receiving the blade element therein,
said handle including a pair of hollow handle sections, with one section spaced between the other section and the head,
said other section receiving the ultrasonic frequency generator therein,
said handle sections being removably attached to one another so that the one section and head can be removed from the other section and ultrasonic frequency generator for sterilization.

40. The ultrasonic dermatome as claimed in claim 22,
said blade assembly further including a proximal booster section drivingly connected between the blade assembly and ultrasonic frequency generator,
said handle including a wall that extends axially along and is in support contact with the booster section, with the booster section being operable to transmit ultrasonic energy between the ultrasonic frequency generator and the blade section and tune the resonant frequency.

* * * * *